(12) United States Patent
Josef et al.

(10) Patent No.: US 9,567,133 B2
(45) Date of Patent: Feb. 14, 2017

(54) WORKPIECE CARRIER FOR TRANSPORTING AND/OR STORING COMPONENTS OF DRUG DELIVERY DEVICES

(71) Applicant: SANOFI-AVENTIS DEUTSCHLAND GMBH, Frankfurt am Main (DE)

(72) Inventors: Clemens Josef, Frankfurt am Main (DE); Christian Simon, Frankfurt am Main (DE); Andreas Bode, Frankfurt am Main (DE); Christian Pommereau, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 15/208,286

(22) Filed: Jul. 12, 2016

(65) Prior Publication Data
US 2016/0332777 A1    Nov. 17, 2016

Related U.S. Application Data

(63) Continuation of application No. 13/696,839, filed as application No. PCT/EP2011/057698 on May 12, 2011, now abandoned.

(30) Foreign Application Priority Data

May 12, 2010 (EP) .................... 10162618

(51) Int. Cl.
*B65D 21/02* (2006.01)
*A61M 5/00* (2006.01)

(52) U.S. Cl.
CPC .......... *B65D 21/0216* (2013.01); *A61M 5/002* (2013.01); *A61M 5/008* (2013.01); *B65D 21/0233* (2013.01); *B65D 21/0235* (2013.01)

(58) Field of Classification Search
CPC .............. B65D 21/045; B65D 21/0212; B65D 21/0216; B65D 21/0226; B65D 21/0233; B65D 71/70; B65D 81/133; B65D 81/203; A61M 5/002; A61M 5/008; B65G 57/00
(Continued)

(56) References Cited

U.S. PATENT DOCUMENTS

| 1,960,279 A | 5/1934 | Read |
| 3,000,528 A | 9/1961 | Kuhl et al. |

(Continued)

FOREIGN PATENT DOCUMENTS

| FR | 2771390 A1 | 5/1999 |
| GB | 2267897 A | 12/1993 |

(Continued)

OTHER PUBLICATIONS

European Search Report for European App. No. 10162618, completed Sep. 27, 2010.
(Continued)

*Primary Examiner* — J. Gregory Pickett
*Assistant Examiner* — Brijesh V. Patel
(74) *Attorney, Agent, or Firm* — McDonnell Boehnen Hulbert & Berghoff LLP

(57) ABSTRACT

The present invention relates to a workpiece carrier for transporting and/or storing components of a drug delivery device, comprising: an array of accommodating recesses extending in a first lateral plane (x, y) and being adapted to receive at least one component of the drug delivery device, at least one stack forming structure adapted to mate with a corresponding stack forming structure of another workpiece carrier for mutually aligning workpiece carriers when stacked on one another, wherein the center of the at least one stack forming structure is arranged laterally offset with respect to the center of the array of accommodating recesses (Continued)

in at least one lateral direction, and wherein the stack forming structure comprises a surrounding edge comprising at least in sections a corrugated or undulated structure.

14 Claims, 4 Drawing Sheets

(58) Field of Classification Search
USPC   206/366, 503–507, 509–510, 821; 220/4.01, 4.26
See application file for complete search history.

(56) References Cited

U.S. PATENT DOCUMENTS

| | | |
|---|---|---|
| 3,272,371 A | 9/1966 | Weiner |
| 3,282,458 A | 11/1966 | Rudd |
| 3,589,511 A | 6/1971 | Britt |
| 3,675,806 A | 7/1972 | Noguchi |
| 3,877,599 A | 4/1975 | Morris |
| 3,997,057 A | 12/1976 | Craig |
| 4,054,207 A | 10/1977 | Lazure et al. |
| 4,101,049 A | 7/1978 | Wallace et al. |
| 4,195,743 A | 4/1980 | Emery |
| 4,349,109 A | 9/1982 | Scordato et al. |
| 4,379,508 A | 4/1983 | Miller et al. |
| 4,438,845 A | 3/1984 | Mochow |
| 5,577,613 A | 11/1996 | Laidlaw |
| 6,007,779 A | 12/1999 | Lemieux et al. |
| 6,079,554 A | 6/2000 | Hammett et al. |
| 6,089,372 A | 7/2000 | Fahrion |
| 6,216,885 B1 | 4/2001 | Guillaume |
| 6,276,531 B1 * | 8/2001 | Andrews ............... B65D 85/32 206/511 |
| 7,909,164 B2 * | 3/2011 | Andrews ............... B65D 85/32 206/521.1 |
| 2008/0115413 A1 | 5/2008 | Blackmore |
| 2010/0243512 A1 | 9/2010 | Hardy |
| 2011/0132789 A1 | 6/2011 | Peng et al. |
| 2012/0317929 A1 | 12/2012 | Ramberg et al. |

FOREIGN PATENT DOCUMENTS

| | | |
|---|---|---|
| JP | 39-003829 Y | 2/1939 |
| JP | 06-001239 U | 11/1994 |
| JP | 2009-23699 A | 2/2009 |
| WO | 96/12657 | 5/1996 |
| WO | 03/020592 | 3/2003 |

OTHER PUBLICATIONS

International Preliminary Report on Patentability for Int. App. No. PCT/EP2011/057698, mailed May 29, 2012.
International Search Report for Int. App. No. PCT/EP2011/057698, completed Aug. 2, 2011.
Japanese Office Action for JP App. No. 2013-509572, mailed Jun. 23, 2015.

* cited by examiner

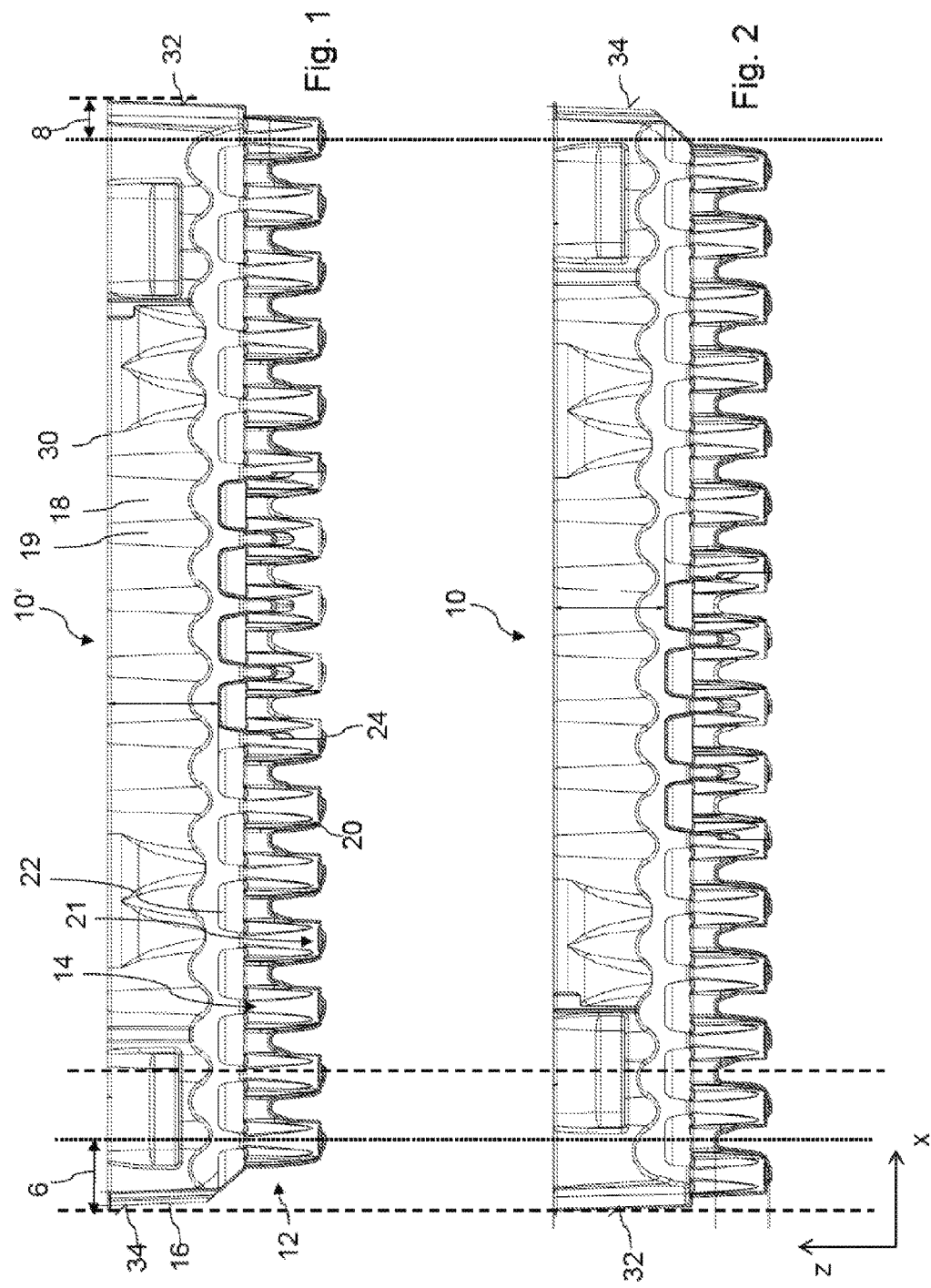

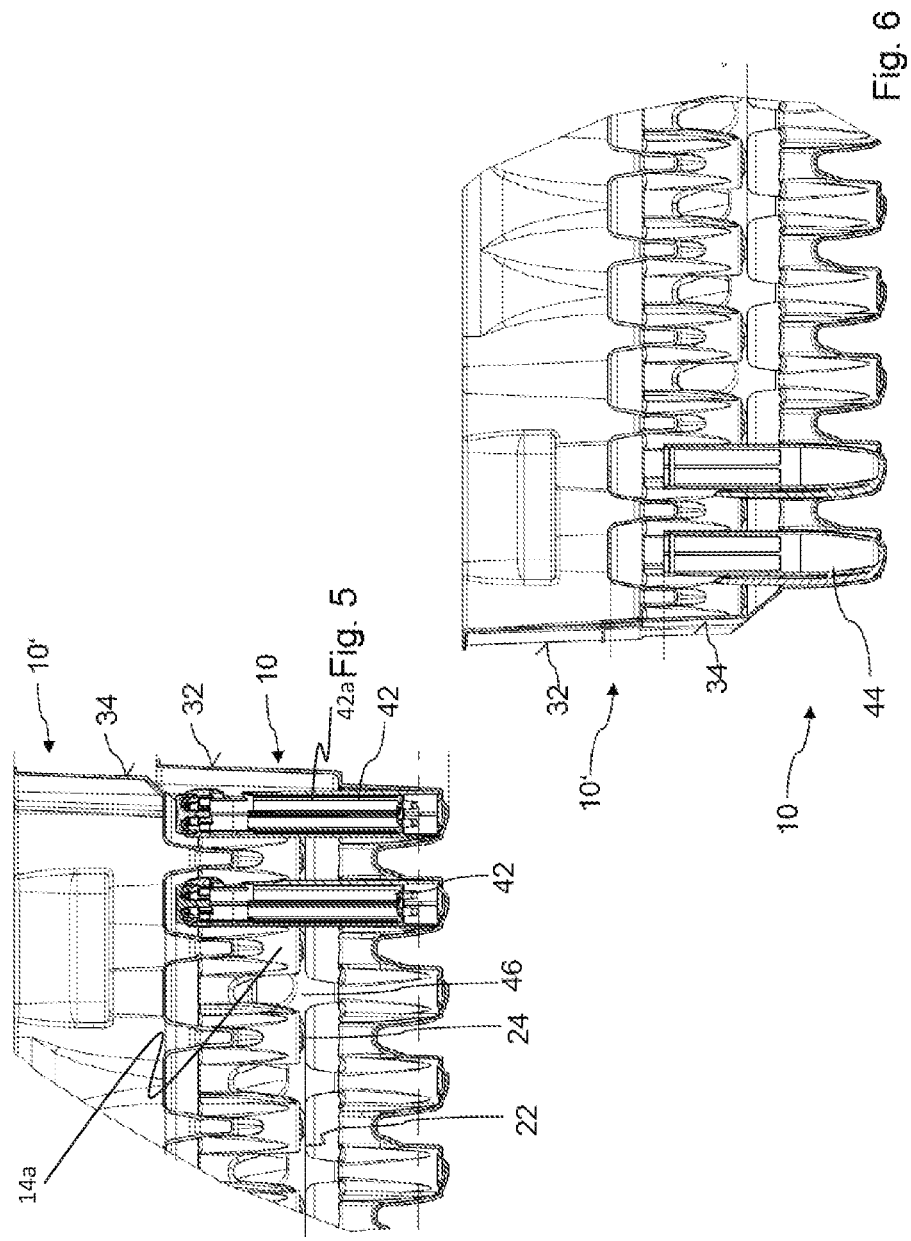

WORKPIECE CARRIER FOR TRANSPORTING AND/OR STORING COMPONENTS OF DRUG DELIVERY DEVICES

CROSS REFERENCE TO RELATED APPLICATIONS

The present application is a continuation of U.S. patent application Ser. No. 13/696,839, filed Mar. 20, 2013, which is a U.S. National Phase Application pursuant to 35 U.S.C. §371 of International Application No. PCT/EP2011/057698 filed May 12, 2011, which claims priority to European Patent Application No. 10162618.2 filed on May 12, 2010. The entire disclosure contents of these applications are herewith incorporated by reference into the present application.

FIELD OF INVENTION

The present invention relates to a workpiece carrier for transporting and/or storing components, in particular sub-assemblies of drug delivery devices, such as pen-type injectors. Moreover, the invention also relates to a workpiece carrier assembly comprising a plurality of workpiece carriers stacked on one another and further refers to a method of transporting or stacking numerous sub-assemblies for drug delivery devices during manufacture and final assembly.

BACKGROUND

Drug delivery devices allowing for multiple dosing of a required dosage of a liquid medicinal product and further providing administration of such liquid drug to a patient, are as such well-known in the prior art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the medicinal product to be administered is provided in a cartridge having a moveable piston or bung mechanically interacting with a piston rod of a drive mechanism of the drug delivery device. By applying thrust to the piston in distal direction, a certain and pre-defined amount of the medicinal fluid is expelled from the cartridge.

Manufacturing and final assembling of such drug delivery devices is implemented in a mass-production process. Typically, various components of the drug delivery device are manufactured and/or even pre-configured by different suppliers. In particular with disposable devices, the cartridge containing the medicament has to be positioned in a respective cartridge holder component prior to a final assembly of cartridge holder and body of the drug delivery device.

In a typical end-assembly scenario two sub-assemblies have to be assembled with each other. For instance, a first sub-assembly comprises a cartridge holder and the cartridge disposed therein. The second sub-assembly comprises a housing or body of the drug delivery device comprising a drive mechanism adapted to become operably engaged with the moveable piston of the cartridge either during assembly or prior to an initial use of the device.

Since the final assembly is conducted almost entirely automatically, the sub-assemblies have to be provided in a well-defined and ordered way. Hence, the sub-assemblies have to be correctly oriented and disposed on a respective support structure.

Such support structures typically comprise a workpiece carrier or transport tray which is adapted to receive a plurality of sub-assemblies and/or components of the drug delivery device.

Optimization of transportation in terms of required storage or shipping space is a persistent aim for reducing costs of manufacture and logistics in mass production processes.

It is an object of the invention to provide an improved workpiece carrier for transporting and/or storing components of a drug delivery device that can be stacked on one another in a space saving way, both, when empty and/or when populated with drug delivery device components. Furthermore, the workpiece carrier should be robust and stable in construction as well as light weight and cost-efficient in production.

SUMMARY

The workpiece carrier according to the present invention is adapted for transporting and/or storing components of a drug delivery device, such as a cartridge holder sub-assembly and/or a body sub-assembly of a drug delivery device that have to be provided to a fully-automatic assembly line in a well-defined, ordered and oriented way. The workpiece carrier therefore comprises an array of accommodating recesses, wherein each of the recesses is adapted to receive a sub-assembly of the drug delivery device, e.g. a cartridge holder or a body component. The recesses are preferably arranged regularly and/or equidistant in an array-like way, wherein the array extends in a lateral plane (x, y). The array extends in two directions (x, y) and defines a support structure for holding and fixing components of the drug delivery at least during a final assembly procedure of the drug delivery device.

The workpiece carrier further comprises at least one stack forming structure adapted to mate with a corresponding stack forming structure of another workpiece carrier for mutually aligning said workpiece carriers when stacked on one another. Stacking direction (z) preferably extends perpendicular to the lateral plane (x, y). The stack forming structure is in particular adapted and designed for mutually aligning stacked workpiece carriers at least with respect to their lateral direction (x, y).

Preferably, the stack forming structure may also be adapted to define the stacking height of the workpiece carriers. In this case, the stack forming structure extends in direction of the surface normal (z) of the plane of the array.

It is even conceivable that the stack forming structure is spaced from the array in the direction of the surface normal of its lateral plane. Hence, array and stack forming structure may extend in different lateral but preferably parallel oriented planes.

The centres and/or outer outer margins of array and stack forming structure are arranged laterally offset with respect to each other in at least one lateral direction. By way of the lateral offset, the relative position and orientation of arrays of accommodating recesses of workpiece carriers being stacked on one another in different orientations, also differs in a corresponding way.

The stack forming structure further comprises a surrounding edge or a circumferential frame that forms a lateral edge or border of the workpiece carrier. Preferably, the surrounding edge comprises at least in sections a corrugated or undulated structure. This way, workpiece carriers stacked on one another in a first configuration can be mutually fixed with respect to each other in the lateral plane (x, y). Moreover, also in a second configuration, wherein adjacently disposed and stacked workpiece carriers are e.g. rotated by 180°, the corrugated or undulated structure of the surrounding edges of adjacently disposed workpiece carriers mutually match and serve to provide a lateral fixing means for the stack of workpiece carriers.

Additionally, the undulated or corrugated structure provides enhanced rigidity and stiffness of the workpiece carrier itself. Also, the corrugations or undulations in the surrounding edge may further serve to guide and to align workpiece carriers of a stack of workpiece carriers in the lateral direction or lateral plan, extending perpendicular to the stacking direction.

The surrounding edge is further adapted to at least partially receive a corresponding surrounding edge of another workpiece carrier when said at least two workpiece carriers are stacked on one another. Shape and geometry of the surrounding edge is such, that identically shape workpiece carriers can be stacked on one another in at least two different mutual orientations. Irrespective on whether the workpiece carriers are stacked on one another according to the first or second orientation, the surrounding edges of first and second workpiece carriers mutually match and at least partially engage with each other.

The surrounding edge is typically designed as a circumferential frame, wherein an inward side wall section of the surrounding edge serves as a receptacle for an outer side wall of a corresponding surrounding edge of another workpiece carrier to be stacked thereon. This way, surrounding edges or circumferential frame portions of a stack of workpiece carriers can be arranged in a nested and in at least partially overlapping way.

Preferably, the vertical dimensions of the accommodating recesses, the surrounding edge and the position of support surfaces between the accommodating recesses is chosen such, that even in the second stack configuration the surrounding edges of workpiece carriers stacked on one another at least partially overlap in the lateral plane (x, y).

Therefore, in a further embodiment the stack forming structure is adapted to enable stacking of workpiece carriers in at least two different mutual orientations. The stack forming structure comprises an internal structure allowing mutual engagement of stack forming structures in different orientations with respect to each other. Preferably, the stack forming structure is at least mirror symmetrical.

Typically, outer and inner dimensions of the stack forming structure mutually match and provide a lateral fixing for workpiece carriers stacked on one another. Shape and geometry of the stack forming structure is such, that identical workpiece carriers can be stacked on one another in at least two different mutual orientations forming different stack configurations.

In a first configuration of at least first and second workpiece carriers, said first and second workpiece carriers are oriented in the same way. In a second configuration, the second workpiece carrier is rotated with respect to the first workpiece carrier in the lateral plane by e.g. 90° or 180°.

Since the array of accommodating recesses is laterally offset with respect to the stack forming structure, in said second configuration, accommodating recesses of first and second workpiece carriers do no longer entirely overlap in the lateral plane and may therefore provide optimized and preferably enlarged storage volume for the components of the drug delivery device.

According to a further preferred embodiment, the lateral offset of stack forming structure and array substantially equals half the distance of adjacently arranged accommodating recesses. Preferably, the accommodating recesses are arranged in a regular row- and column-wise manner, wherein rows of accommodating recesses extend in one lateral direction (x) and columns of accommodating recesses extend in the other lateral direction (y). When the lateral offset substantially equals half the distance of adjacently arranged accommodating recesses, by stacking workpiece carriers on one another in different mutual orientations, accommodating recesses of a first workpiece carrier will overlap with interstices between accommodating recesses of a second workpiece carrier as seen in the lateral plane.

Consequently, by stacking workpiece carriers in different mutual orientations on one another, relative position of accommodating recesses of adjacently arranged workpiece carriers can be modified in at least one lateral direction.

In a further preferred embodiment, the stack forming structure and the array of accommodating recesses are arranged laterally offset in both transverse directions (x, y). The lateral offset can for instance be defined as the lateral distance between the centre of the stack forming structure and a corresponding centre of the array of accommodating recesses.

By having respective centres of array and stack forming structure displaced in both lateral directions, the position of accommodating recesses of workpiece carriers stacked on one another in different mutual orientations varies with respect to both lateral directions (x, y).

In another preferred aspect, the accommodating recesses are regularly spaced with respect to each other in both lateral directions (x, y). In particular, lateral distance of adjacently arranged accommodating recesses in x-direction is substantially identical to the distance of the adjacently arranged accommodating recesses in y-direction, wherein x- and y-direction are substantially perpendicular to each other.

In a further preferred aspect, each of the accommodating recesses comprises a tapered or conical pocket hole forming a protrusion at a bottom side of the workpiece carrier. As seen from the top of the workpiece carrier, the accommodating recesses are designed as a depression forming a protrusion on the opposite lower side of the workpiece carrier. Furthermore, when workpiece carriers are stacked on one another in identical orientation, the array of accommodating recesses is adapted to receive an array of corresponding protrusions of another workpiece carrier stacked thereon. In this way, stacking height of a stack of workpiece carriers can be reduced to a minimum when corresponding accommodating recesses and protrusions are arranged in an at least partially nested way.

The accommodating recesses preferably extend in vertical direction with respect to the plane of the workpiece carrier and its array of accommodating recesses. In particular when designed as a carrier for parts or sub-assemblies of e.g. pen-type injectors or similar medical devices, the various device components can arranged and stored in the recesses in an upright way. For instance, a sub-assembly or a housing component of a drug delivery device may point in a direction substantially perpendicular to the plane defined by the array of accommodating recesses.

In a further preferred embodiment, the array of accommodating recesses comprises a plurality of support surfaces arranged between adjacently located accommodating recesses. The support surfaces are further adapted to serve as a support for corresponding protrusions of another workpiece carrier stack thereon in a second orientation or configuration. By way of the support surfaces of a lower workpiece carrier and the downward pointing protrusion at a bottom side of another workpiece carrier, a mutual abutment configuration can be attained, in which a particular component of a drug delivery device, e.g. a sub-assembly such as a cartridge holder can be positioned into an accommodating recess with a lower part while its upper part extends between downward pointing protrusion of another workpiece carrier stacked thereon.

This supports surfaces further allow to stack a plurality of workpiece carriers on top of each other in such a way, that the accommodating recesses formed therebetween are larger than the components to be stored therein. In other words, by way of the support surfaces and corresponding protrusions of an adjacently located workpiece carrier, even a stacked configuration can be attained without the necessity of having a component of a drug delivery device arranged in or on the accommodating recesses. Since the protrusions and support surfaces serve as mutually corresponding posts that get in direct contact with each other even when workpiece carriers are arranged on top of each other, the stacking height of multiple workpiece carriers is only and exclusively governed by the geometry of the protrusions and their corresponding support surfaces. This way, workpiece carriers can be stacked on top of each other in a stable way even when only partially filled or loaded with components. The filling or storing status of the workpiece carriers has therefore no influence on the stacking configuration or stacking height.

Preferably, the interstices between the protrusions at a bottom side of the workpiece carrier are adapted to receive an upper part of a drug delivery component that is disposed in an accommodating recess of a workpiece carrier disposed underneath.

Since the accommodating recesses comprise a tapered shape towards their lower end section, the device components can be releasably secured therein, e.g. by way of clamping.

In a further preferred embodiment of the invention, first and second orientations of the workpiece carrier are transferable into each other by a rotation of the workpiece carrier by 180° in the lateral plane. Hence, the workpiece carrier has to be rotated around its surface normal, preferably with respect to the centre of the at least one stack forming structure.

In the second configuration, in which every second workpiece carrier is rotated by substantially 180° with respect to its surface normal, the stacking height increases since downward pointing protrusions at a bottom side of an upper workpiece carrier get in mutual abutment with interstitial support surfaces of another workpiece carrier disposed underneath. In this configuration, protrusions of an upper workpiece carrier substantially overlap with support surfaces arranged between accommodating recesses of a lower workpiece carrier. Correspondingly, interstices between the downward pointing protrusions of the upper workpiece carrier substantially overlap with accommodating recesses of a lower workpiece carrier in a projection of the lateral plane (x, y).

According to a further preferred embodiment, the surrounding edge at its upper end at least in sections comprises an outward extending flange portion. The flange portion also provides enhanced stiffness and rigidity. Additionally, the outward extending upper flange portion may provide a support and an abutment means for workpiece carriers to be stacked thereon.

In a further preferred aspect, the flange portion almost entirely surrounds the surrounding edge and comprises at least two gripping recesses. Hence, the circumferential flange portion is interrupted or broken by the at least two gripping recesses. By way of the gripping recesses, a plurality of workpiece carriers can even be arranged next to each other in configuration of a mutual lateral abutment. By way of the gripping recesses, a particular workpiece carrier can be gripped from above, since the gripping recesses provide access for a corresponding gripping tool to lift a particular workpiece carrier.

In a further preferred embodiment, the surrounding edge comprises at least one outwardly extending projection having an inward directed ledge at its lower end. This ledge is adapted to but against a flange portion of another workpiece stacked beneath in the first orientation or configuration. With mutually interacting and mutually abutting ledge and flange portions of an upper and lower workpiece carrier stacked onto each other in the first configuration, a minimum stacking height can be attained and disassembling of stacked workpiece carriers can be facilitated.

Otherwise, when a larger number of empty workpiece carriers is stacked on one another, the workpiece carriers may otherwise tend to frictionally engage under the effect of e.g. gravitational forces.

In a further preferred embodiment, the workpiece carrier is made of a thermoplastic material either by way of injection moulding or by way of deep-drawing and combinations thereof. Preferably, the die forming the accommodating recesses is located at a lower position compared to a downward acting punch which in turn is adapted to draw the thermoforming material over the die in a downward direction. Said deep-drawing configuration is such, that the die comprises upward facing protrusions forming the accommodating recesses for the components of the drug delivery device.

In a further preferred aspect, the workpiece carrier is at least partially equipped and populated with at least one sub-assembly of a drug delivery device. The sub-assembly comprises a housing component of the drug delivery device, such as a protective cap, a cartridge holder and/or a body component of the drug delivery device. Preferably, the workpiece carrier is equipped with the sub-assembly of the drug delivery device accommodating a cartridge sealed by a moveable piston and containing a medicament to be dispensed by the drug delivery device after its final assembly.

In another independent aspect, the invention further relates to a workpiece carrier assembly comprising at least a first and a second workpiece carrier as described above. First and second workpiece carriers are of identical shape and geometry and they are stackable on one another in at least two different orientations with different stacking height. In a further configuration, first and second workpiece carriers are oriented in the same direction allowing for a minimum stacking height when stacked on one another. In a second configuration, every second workpiece carrier is oriented differently with respect to its neighbouring workpiece carrier of a workpiece carrier stack.

In this configuration, downward pointing protrusions corresponding with accommodating recesses of an upper workpiece carrier but against support surfaces of a lower workpiece carrier located between said carrier's accommodating recesses. Hence, the stacking height will increase. However, in this configuration, the stacking height can be smaller than the size, in particular the vertical extension of the component of the drug delivery device disposed in the accommodating recesses. Typically, the extension of the accommodating recesses is smaller than the vertical extension of the components to be disposed therein.

In the second configuration of the workpiece carrier assembly, the upper portion of the device component protruding upwardly from the accommodating recess will be received by a mutually corresponding interstice between downward pointing protrusions of an upper workpiece carrier.

In still another aspect, the invention also provides a method for transporting and/or for storing numerous sub-assemblies of a drug delivery device by making use of at least two workpiece carriers as described above. Here, empty workpiece carriers are stacked on one another according to a first configuration, in which adjacently disposed workpiece carriers are oriented in the same direction. During or after populating the at least two or more workpiece carriers with numerous sub-assemblies of the drug delivery device, first and second workpiece carriers are stacked on one another in a second configuration by rotating every second workpiece carrier by substantially 180° with respect to its surface normal, preferably with a centre of a stack forming structure, e.g. of a surrounding edge as axis of rotation.

In this way, package density for both, empty workpiece carriers as well as for workpiece carriers populated with components of the drug delivery device can be increased.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described by making reference to the Figures in which:

FIG. 1 shows a cross section in the z-x-plane of a workpiece carrier in a first orientation and FIG. 2 shows the workpiece carrier according to FIG. 1 in a rotated, second orientation, FIG. 5 is illustrative of two workpiece carriers stacked on one another in a second configuration receiving a first sub-assembly of a drug delivery device and FIG. 6 shows another stack of two workpiece carriers supporting a second sub-assembly of the drug delivery device.

DETAILED DESCRIPTION

Figure 3:
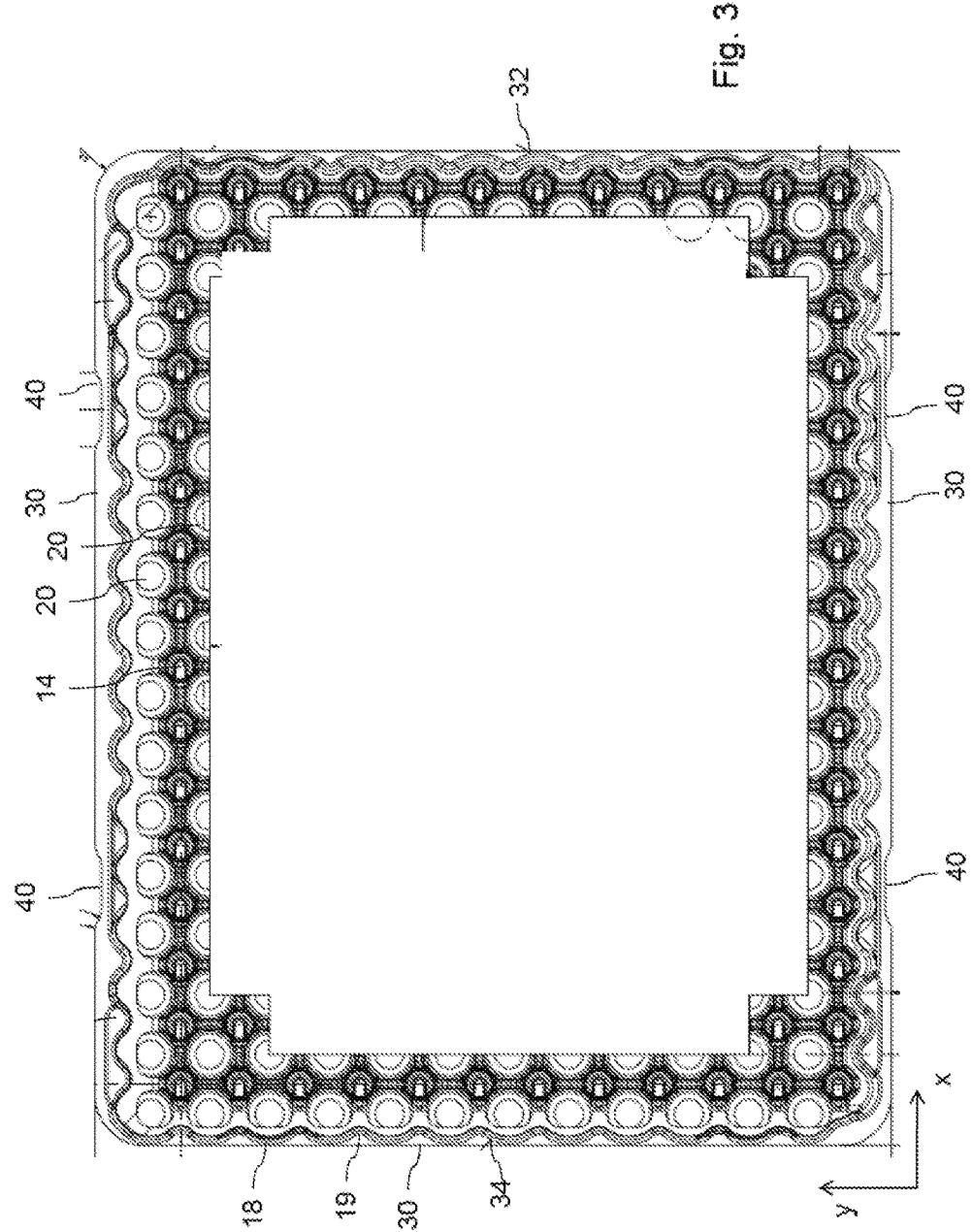
FIG. 3 is schematically illustrative of a top view of the workpiece carrier.

The workpiece carrier 10 as illustrated in FIGS. 1 to 3 comprises an array 12 of regularly row- and column-wise arranged accommodating recesses 14 which extend downwardly and form respective downward pointing protrusion 20 at the bottom side of the respective workpiece carrier 10. The array of accommodating recesses 14 extends in a lateral plane (x, y) as illustrated in FIG. 3. Between adjacently located accommodating recesses 14 a support surface 22 extends comprising a flattened shape. The support surface 20 is of substantially circular shape while the recesses 14 comprise a substantially hollow cylindrical structure, preferably at least slightly conically converging or tapering towards their lower free end 24.

The accommodating recesses 14, and their corresponding protrusion 20 extending from the bottom side of the workpiece carrier 10 comprise a flattened or rounded free end 24. As further illustrated in FIG. 1, the surrounding edge 16 serving as a stack forming structure comprises a left side wall section 34 and a right side wall section 32, both of corrugated or undulated structure 18, 19. The surrounding edge 16 is further vertically displaced from the array 12 of accommodating recesses 14.

As illustrated in FIG. 1, the left side edge 34 of the surrounding edge 16 is spaced apart from the centre of a first adjacently located accommodating recess 14 by a first distance 6 whereas the right side edge 32 is spaced apart from the centre of a corresponding outermost accommodating recess 14 by a distance 8. The difference in the two distances 6, 8 substantially equals half the distance between adjacently disposed recesses 14 in lateral direction (x). Even though not illustrated, the same applies for the other lateral direction (y). Hence, the array 12 of accommodating recesses 14 is laterally offset with respect to the surrounding edge 16, which becomes apparent by a comparison of FIGS. 1 and 2.

The workpiece carrier 10 according to FIG. 2 is rotated by 180° with respect to the z-axis with the centre of the surrounding edge 16 as axis of rotation. Consequently, as illustrated by the vertical dotted line, surrounding edges 16 of the workpiece carriers 10 of FIGS. 1 and 2 are aligned with each other, whereas the lateral positions of the accommodating recesses 14 of the workpiece carrier 10 according to FIG. 1 substantially overlap with support surfaces 22 of the workpiece carrier according to FIG. 2.

Figure 4:
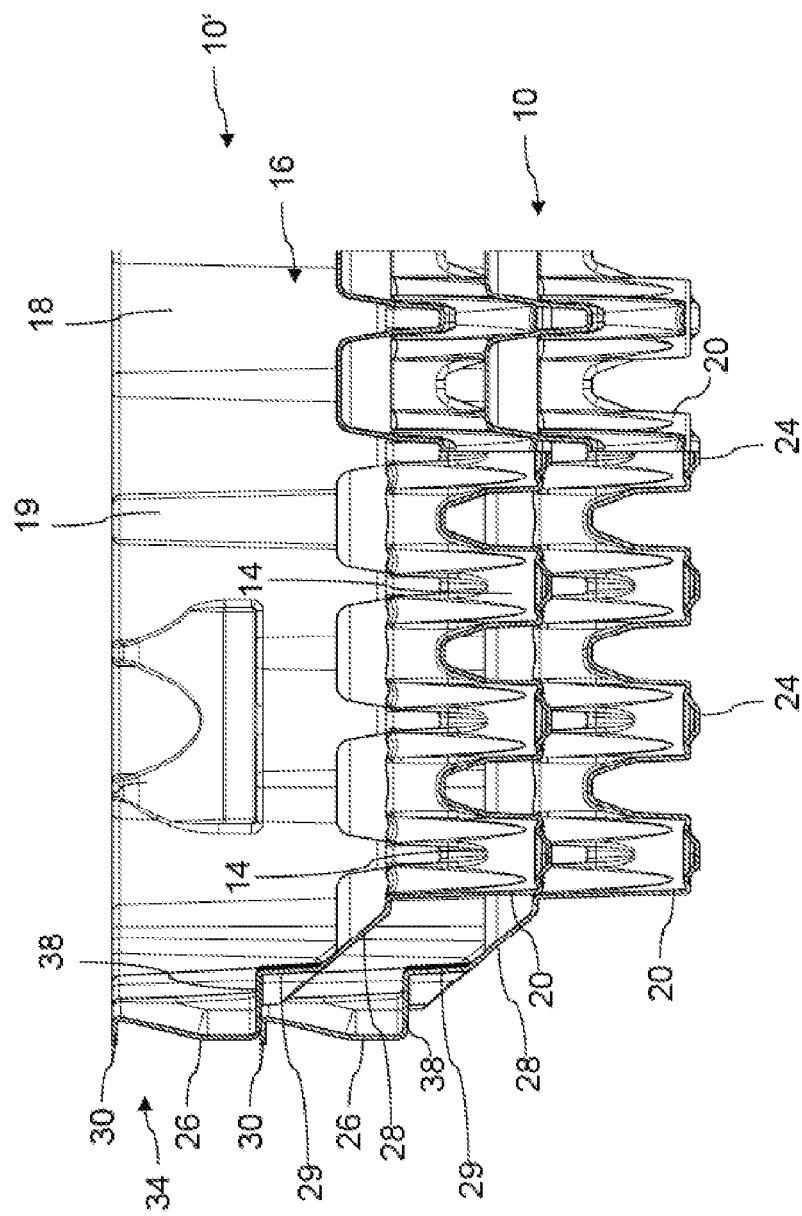
FIG. 4 shows an enlarged cross-section of two workpiece carriers stacked on one another in a first configuration.

Accordingly, if workpiece carriers 10 are stacked on one another in their first configuration, in which the workpiece carriers 10 are oriented in the same way, downward pointing protrusions 20 at a bottom side of an upper workpiece carrier 10' will engage with the accommodating recesses 14 of a lower workpiece carrier 10 stacked underneath as shown for example in FIG. 4.

Since the accommodating recesses 14 comprise a downward extending tapered pocket hole 14a mutual engagement of protrusions 20 and recesses 14 is preferably delimited in order to facilitate disassembling of a stack of workpiece carriers. For this purpose, the workpiece carrier 10 comprises an outward extending flange portion 30 at an upper end section of its surrounding edge 16. Additionally, the edge 16 comprises at least one outwardly extending projection 26 having an inward directed ledge 38 at its lower end.

In a stacked configuration as shown in FIG. 4, the lower and inward directed ledge 38 extending inwardly from an outwardly protruding projection 26 of the upper workpiece carrier 10' buts against the outwardly extending flange portion 30 of the lower workpiece carrier 10 in vertical direction. In this way, nested arrangement of upper and lower workpiece carriers 10', 10 can be confined. The projection 26 with its laterally extending ledge 38 is provided at opposite side edges 32, 34 of the carrier. They further correspond with the projections 26 disposed at side edges interconnecting left and right side edges 32 and 34.

The horizontally extending ledge 38 disposed at the lower end of the projection 26 extends into a substantially vertically and downward extending side edge portion 29, which in turn extends to the outermost protrusion 20 via a bevelled side face portion 28.

By way of the bevelled side face 28, a mutual stacking and aligning of a multiplicity of workpiece carriers in the lateral plane (x, y) can be simplified. However, in alternative embodiment the slanted side face portion 28 can also be replaced by another substantially horizontally extending side wall portion, being not further illustrated here.

Turning the upper workpiece carrier 10' by 180°, such that the corrugated or undulated side wall 32 of the upper workpiece carrier 10' faces towards the opposite side wall section 34 of a lower workpiece carrier 10, another, second nested configuration as illustrated in FIGS. 5 and 6 can be attained. As illustrated there, the lower free end sections 24 of downward pointing protrusions 20 of accommodating recesses 14 of the upper workpiece 10' but against corresponding support surfaces 22 of the lower workpiece carrier 10.

This way, the effective volume of the recesses 14 is enlarged in an upward direction by the interstices 46 formed between the downward directed protrusions 20 of the upper workpiece 10'. As further illustrated in FIG. 5, the accommodating recess 14 of the lower workpiece carrier 10 and the corresponding interstices at the bottom of the upper workpiece carrier 10' form a combined receptacle for a subassembly 42 of the drug delivery device having a housing component 42a (see FIG. 5).

In FIG. 6, a corresponding nested and stacked arrangement of a lower and an upper workpiece carrier 10, 10' is illustrated. Here, the accommodating recesses 14 are partially populated with a cartridge holder sub-assembly 44 of the drug delivery device further comprising the cartridge being filled with the medicament.

The undulations 18, 19 of the surrounding edge 16 are best illustrated in FIG. 3. The undulations 18, 19 are designed such, that an outwardly protruding undulating portion 18 always matches with an undulating recess 19 irrespective on the mutual orientation of workpiece carriers in the lateral plane (x, y). By way of the undulations, empty workpiece carriers can be stacked on one another in a well-defined way.

It is to be noted, that for reasons of simplicity FIG. 3 only reflects an outer portion of the array 12 of accommodating recesses 14, that be evenly distributed over the entire plane (x, y) of the array 12. In FIG. 3 also the outward extending flange 30 is shown being interrupted by four gripping recesses 40 that allow to selectively grip one of a plurality of workpiece carriers disposed next to each other even when their outer flanges 30 are in direct contact with each other.

The invention claimed is:

1. A workpiece carrier for transporting or storing components of a drug delivery device, comprising:
   an array of accommodating recesses extending in a first lateral plane (x, y) and being adapted to receive at least one component of the drug delivery device,
   at least one stack forming structure formed to mate with a corresponding stack forming structure of another workpiece carrier for mutually aligning workpiece carriers when stacked on one another,
   wherein the center of the at least one stack forming structure is arranged laterally offset with respect to the center of the array of accommodating recesses in at least one lateral direction (x, y), and
   wherein the stack forming structure extends in a direction of the surface normal (z) of the plane of the array of accommodating recesses and comprises a surrounding edge forming a lateral border of the workpiece carrier and having a left side wall section and a right side wall section both of corrugated or undulated structure and
   wherein an inward side wall section of a first workpiece carrier receives an outer side wall section of a corresponding surrounding edge of a second and identical workpiece carrier to be stacked thereon, and
   wherein the stack forming structure is adapted to enable stacking of a first and second workpiece carriers in at least two different configurations, wherein in a first configuration first and second workpiece carriers are oriented in the same way and wherein in a second configuration the second workpiece carrier is rotated with respect to the first workpiece carrier in the lateral plane (x, y) is rotated by 90° or 180°.

2. The workpiece carrier according to claim 1, wherein an outwardly protruding undulating structure of the first workpiece carrier always engages with a recessed undulating structure of the second workpiece carrier when the first workpiece carrier is in the first configuration and when in the second configuration.

3. The workpiece carrier according to claim 1, wherein the lateral offset of the stack forming structure and array equals half the distance of adjacently arranged accommodating recesses.

4. The workpiece carrier according to claim 1, wherein the stack forming structure and the array are arranged laterally offset in both transverse directions (x, y).

5. The workpiece carrier according to claim 1, wherein each of the accommodating recesses comprises a tapered pocket hole forming a protrusion at a bottom side of the workpiece carrier.

6. The workpiece carrier according to claim 5, wherein the array of accommodating recesses is formed to receive an array of corresponding protrusions of another workpiece carrier stacked thereon in the first orientation.

7. The workpiece carrier according to claim 5, wherein the array comprises support surfaces arranged between adjacently located accommodating recesses and being adapted to serve as a support for corresponding protrusions of another workpiece carrier stacked thereon in the second orientation.

8. The workpiece carrier according to claim 6, wherein the first and second orientations are transferable into each other by a rotation of the workpiece carrier by 180° in the lateral plane (x, y).

9. The workpiece carrier according to claim 1, wherein the surrounding edge has an upper end where at least in sections comprises an outward extending flange portion.

10. The workpiece carrier according to claim 9, wherein the flange portion entirely surrounds the surrounding edge and comprises at least two gripping recesses.

11. The workpiece carrier according to claim 1, wherein the stack forming structure comprises at least one outwardly extending projection having an inward directed ledge on a lower end formed to abut against a flange portion of another workpiece carrier stacked beneath in the first orientation.

12. The workpiece carrier according to claim 1, comprising at least one sub-assembly of a drug delivery device, wherein the sub-assembly comprises a housing component of the drug delivery device.

13. A workpiece carrier assembly comprising at least a first and a second workpiece carrier according to claim 1, wherein first and second workpiece carriers are stackable on one another in at least two different orientations with different stack height.

14. A method for transporting or storing numerous sub-assemblies for drug delivery devices by making use of at least two workpiece carriers according to claim 1, wherein empty workpiece carriers are stacked on one another in a first configuration in which the workpiece carriers are oriented the same way and wherein workpiece carriers equipped with numerous sub-assemblies of the drug delivery device are stacked on one another in a second configuration by rotating every second workpiece carrier of a stack by 180° with its surface normal as axis of rotation.

* * * * *